(12) United States Patent
Tyber et al.

(10) Patent No.: US 12,144,531 B2
(45) Date of Patent: Nov. 19, 2024

(54) LAPIDUS SCREW GUIDE ASSEMBLY AND METHOD OF INSERTION

(71) Applicant: Tyber Medical LLC, Bethlehem, PA (US)

(72) Inventors: Jeffrey Tyber, Breinigsville, PA (US); Chandler Kline, Lancaster, PA (US); Matthew Atoulikian, Basking Ridge, NJ (US)

(73) Assignee: Tyber Medical LLC, Bethlehem, PA (US)

( * ) Notice: Subject to any disclaimer, the term of this patent is extended or adjusted under 35 U.S.C. 154(b) by 245 days.

(21) Appl. No.: 17/829,429

(22) Filed: Jun. 1, 2022

(65) Prior Publication Data

US 2022/0287755 A1 Sep. 15, 2022

Related U.S. Application Data

(63) Continuation of application No. 17/108,168, filed on Dec. 1, 2020, now Pat. No. 11,389,221, which is a
(Continued)

(51) Int. Cl.
*A61B 17/88* (2006.01)
*A61B 17/17* (2006.01)
(Continued)

(52) U.S. Cl.
CPC ...... *A61B 17/8872* (2013.01); *A61B 17/1739* (2013.01); *A61B 17/1775* (2016.11); *A61B 17/68* (2013.01); *A61B 17/808* (2013.01); *A61B 17/8095* (2013.01); *A61B 17/86* (2013.01); *A61F 2/4606* (2013.01); *A61B 2017/565* (2013.01); *A61B 2017/681* (2013.01); *A61B 17/8061* (2013.01); *A61B 17/863* (2013.01); *A61B 17/8875* (2013.01); *A61B 17/90* (2021.08)

(58) Field of Classification Search
CPC ............ A61B 17/1739; A61B 17/1775; A61B 2017/681; A61B 17/8095; A61B 17/88; A61B 17/8872; A61B 2017/90; A61F 2/4603; A61F 2/4606; A61F 2/4637; A61F 2002/4687
See application file for complete search history.

(56) References Cited

U.S. PATENT DOCUMENTS

| | | | | |
|---|---|---|---|---|
| 2016/0015426 A1* | 1/2016 | Dayton | .................. | A61B 17/66 606/57 |
| 2016/0030064 A1* | 2/2016 | Dacosta | ............. | A61B 17/1725 606/105 |

(Continued)

*Primary Examiner* — Larry E Waggle, Jr.
(74) *Attorney, Agent, or Firm* — Joseph E. Maenner; Maenner & Associates, LLC

(57) ABSTRACT

A screw guide assembly includes a guide body extending along a central longitudinal axis. The guide body has a proximal end portion having an attachment face extending perpendicular to the longitudinal axis and a distal end portion having a screw support member extending away from the longitudinal axis. The screw support member is configured to allow for the insertion of a screw at an angle oblique relative to the longitudinal axis. A wire guide is removably inserted into the screw support member. A method of inserting a screw using the assembly is also disclosed.

17 Claims, 15 Drawing Sheets

Related U.S. Application Data continuation of application No. 16/201,144, filed on Nov. 27, 2018, now Pat. No. 10,888,365, which is a continuation-in-part of application No. 15/646,497, filed on Jul. 11, 2017, now Pat. No. 10,383,737, which is a continuation-in-part of application No. 15/213,935, filed on Jul. 19, 2016, now Pat. No. 10,058,431, which is a continuation-in-part of application No. 15/162,657, filed on May 24, 2016, now Pat. No. 10,369,251, which is a continuation-in-part of application No. 14/948,322, filed on Nov. 22, 2015, now Pat. No. 10,201,433, which is a continuation-in-part of application No. 14/513,300, filed on Oct. 14, 2014, now Pat. No. 10,864,081, which is a continuation-in-part of application No. 14/054,100, filed on Oct. 15, 2013, now Pat. No. 9,387,087.

(60) Provisional application No. 61/715,891, filed on Oct. 19, 2012.

(51) Int. Cl.
| | | |
|---|---|---|
| *A61B 17/68* | (2006.01) | |
| *A61B 17/80* | (2006.01) | |
| *A61B 17/86* | (2006.01) | |
| *A61F 2/46* | (2006.01) | |
| *A61B 17/56* | (2006.01) | |
| *A61B 17/90* | (2006.01) | |

(56) References Cited

U.S. PATENT DOCUMENTS

2017/0014173 A1* 1/2017 Smith ............... A61B 17/1775
2017/0333102 A1* 11/2017 Peterson ........... A61B 17/1717

* cited by examiner

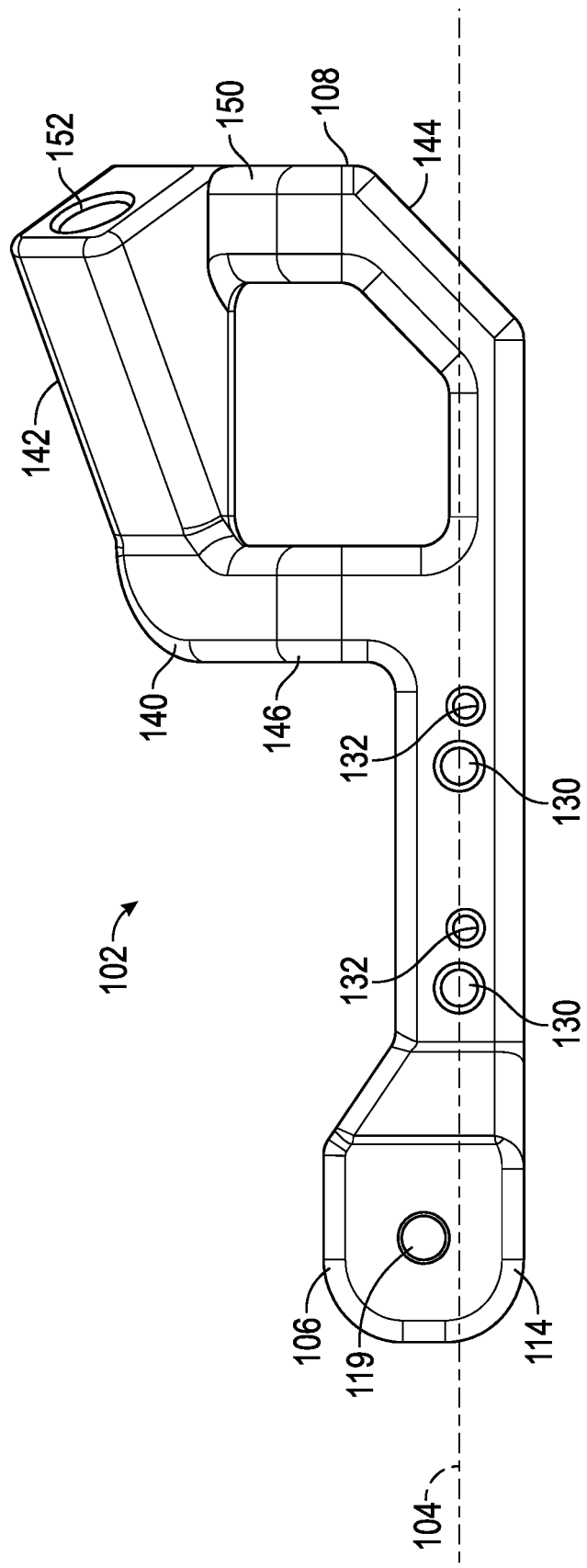

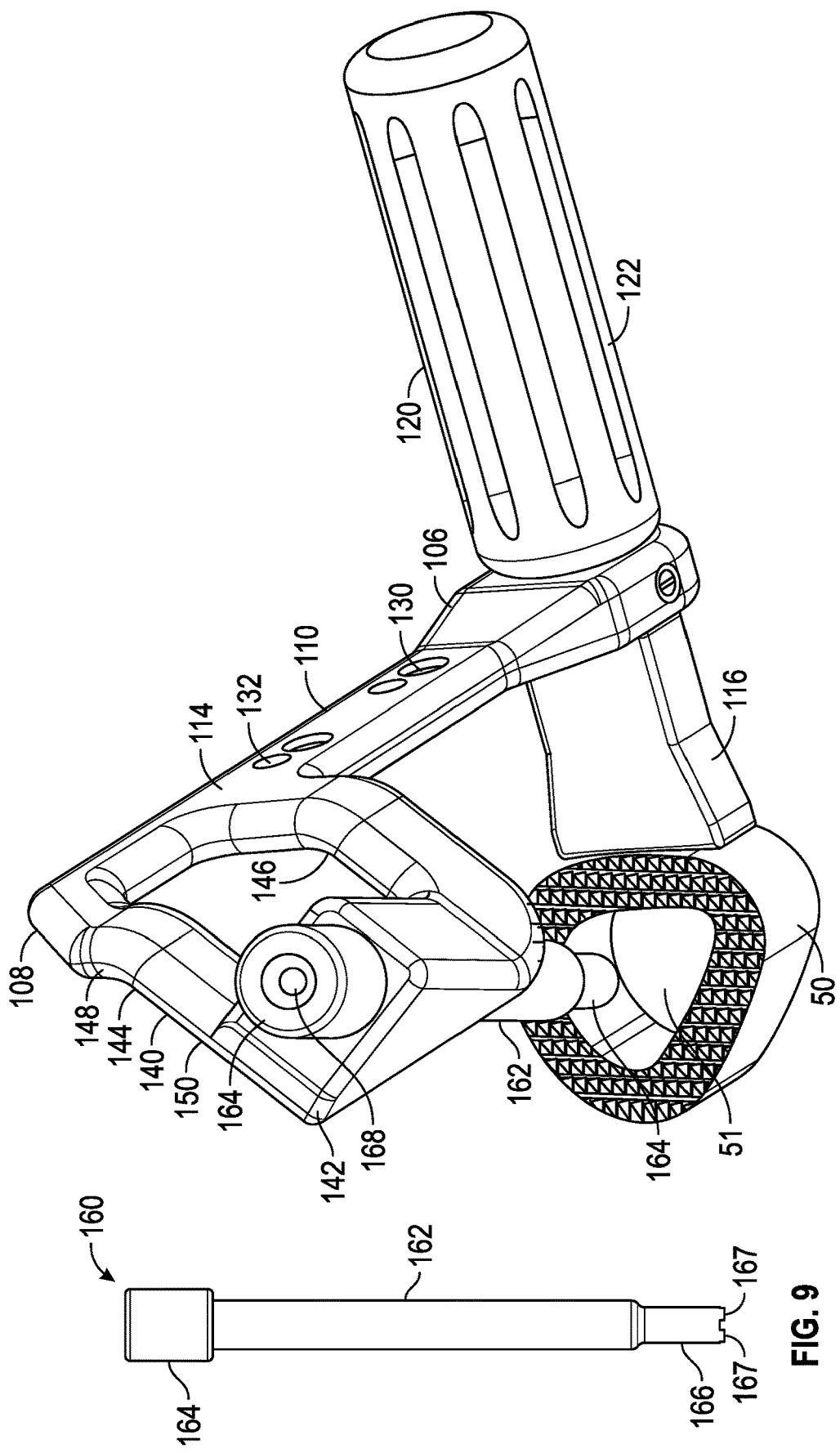

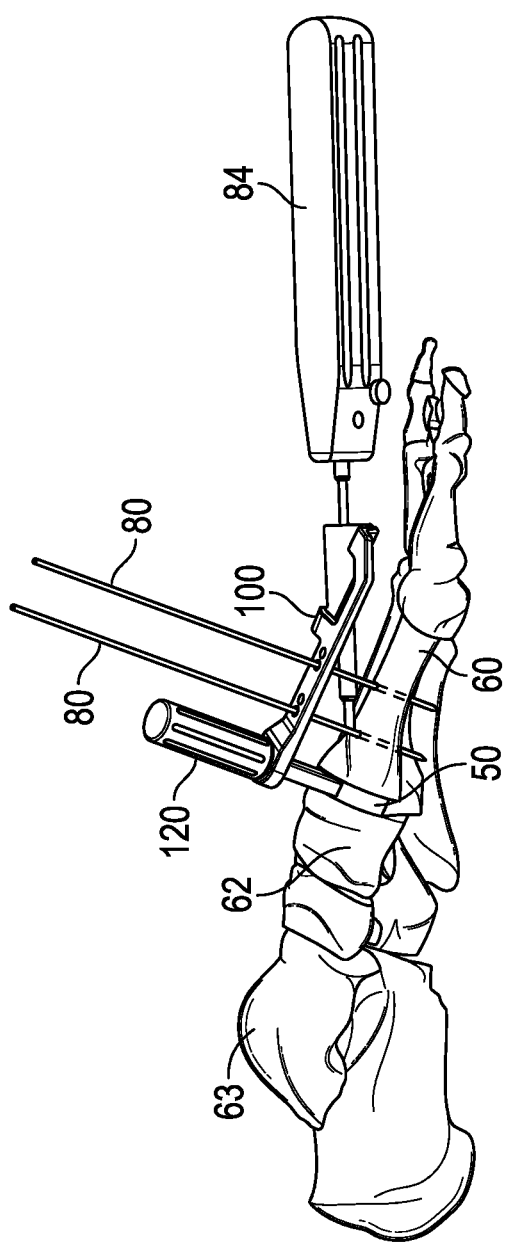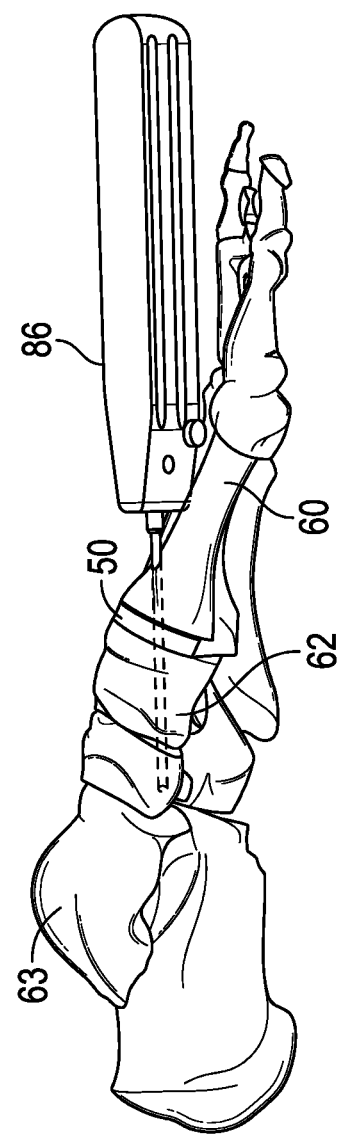
FIG. 23
FIG. 24

LAPIDUS SCREW GUIDE ASSEMBLY AND METHOD OF INSERTION

CROSS-REFERENCE TO RELATED APPLICATIONS

The present application is a continuation of co-pending application Ser. No. 17/108,168, filed on Dec. 1, 2020, which is a continuation of application Ser. No. 16/201,144, filed on Nov. 27, 2018 and issued on Jan. 12, 2021 as U.S. Pat. No. 10,888,365, which is a continuation-in-part of application Ser. No. 15/646,497, filed on Jul. 11, 2017 and issued on Aug. 20, 2019 as U.S. Pat. No. 10,383,737, which is a continuation-in-part of application Ser. No. 15/213,935, filed on Jul. 19, 2016 and issued on Aug. 28, 2018 as U.S. Pat. No. 10,058,431, which is a continuation-in-art of application Ser. No. 15/162,657, filed on May 24, 2016 and issued on Aug. 6, 2019 as U.S. Pat. No. 10,369,251, which is a continuation-in-part of application Ser. No. 14/948,322, filed on Nov. 22, 2015 and issued on Feb. 12, 2019 as U.S. Pat. No. 10,201,433, which is a continuation-in-part of co-pending application Ser. No. 14/513,300, filed on Oct. 14, 2014, which is a continuation-in-part application of U.S. patent application Ser. No. 14/054,100, filed on Oct. 15, 2013 and issued on Jul. 12, 2016 as U.S. Pat. No. 9,387,087, which claims priority from U.S. Provisional Patent Application Ser. No. 61/715,891, filed on Oct. 19, 2012, all of which are incorporated by reference herein in their entireties.

BACKGROUND OF THE INVENTION

Field of the Invention

The present invention relates to an assembly and a method for aligning and inserting a screw into two bone portions to provide alignment and compression.

Description of the Related Art

Due to their weight bearing nature, foot bones are subject to severe stresses and strains as well as diseases, such as arthritis, throughout a person's life. These issues can result in bone deformities. While Evans and Cotton osteotomies are well recognized procedures to correct some of these deformities, these procedures do not allow the metatarsal to be re-aligned or rotated if the metatarsal has moved or rotated out of alignment. It would be beneficial to provide a device and a method for implanting an osteotomy implant while being able to rotate the metatarsal to a proper position.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one embodiment, the present invention is a screw guide assembly. The assembly includes a guide body extending along a central longitudinal axis. The guide body has a proximal end portion having an attachment face extending perpendicular to the longitudinal axis and a distal end portion having a screw support member extending away from the longitudinal axis. The screw support member is configured to allow for the insertion of a screw at an angle oblique relative to the longitudinal axis. A wire guide is removably inserted into the screw support member.

In another embodiment, the invention provides a screw guide assembly comprising an elongate body having a proximal end portion adapted to releasably connect to an implant and a distal end portion, distal from the proximal end portion. An outrigger extends from the distal end portion and a wire guide is removably inserted into the outrigger.

In still another embodiment, the present invention provides a screw guide assembly comprising a generally planar body having a proximal end portion adapted to releasably engage an implant and a distal end portion having at least one arm extending away therefrom. An outrigger is attached to the at least one arm. The outrigger has a through-opening adapted to guide a screw. A wire guide removably inserted into the through-opening.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIG. 4 is a top plan view of the screw guide of FIG. 3;

FIG. 9 is a side elevational view of a wire guide for use with the screw guide of FIG. 3;

FIG. 10 is a distal perspective view of the screw guide assembly of FIG. 1 attached to an implant.

FIG. 23 is a side elevational view of a drill being inserted over the K-wire with the screw wire guide having been removed;

FIG. 24 is a side elevational view of the screw guide assembly having been removed and a countersink drill slid over the K-wire;

DETAILED DESCRIPTION

Figure 1:
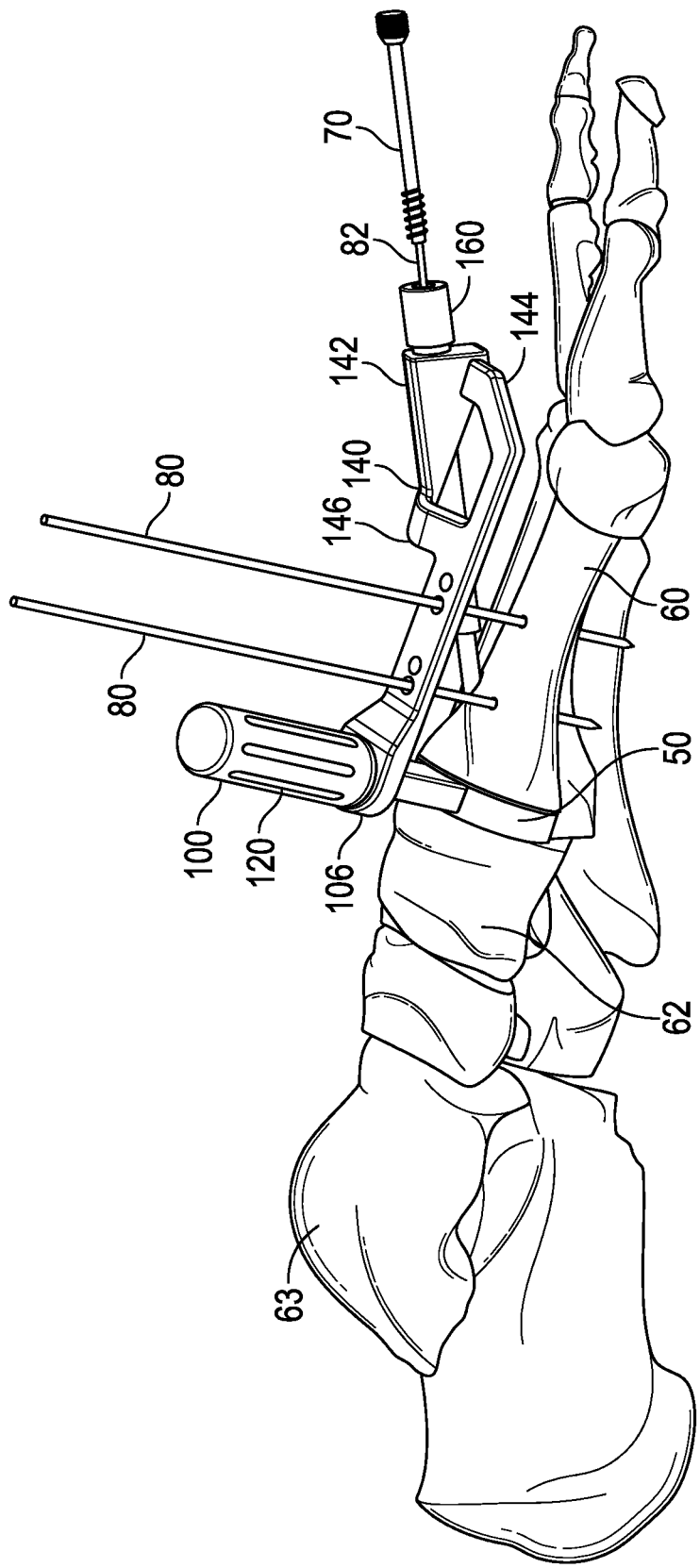
FIG. 1 is a side elevational view of a screw guide assembly according to the present invention attached to a foot bone for screw insertion.
Figure 3:
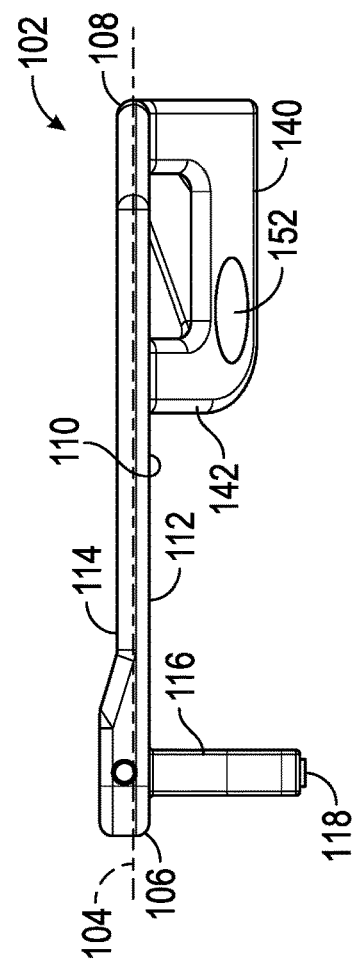
FIG. 3 is a side elevational view of a screw guide used with the screw guide assembly of FIG. 1.

In the drawings, like numerals indicate like elements throughout. Certain terminology is used herein for convenience only and is not to be taken as a limitation on the present invention. The terminology includes the words specifically mentioned, derivatives thereof and words of similar import. As used herein, the term "proximal" is defined as a location closer to the heel of the patient into whom an implant is being inserted and the term "distal" is defined as a location farther from the heel of the patient into whom an implant is being inserted.

The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Unless explicitly stated otherwise, each numerical value and range should be interpreted as being approximate as if the word "about" or "approximately" preceded the value of the value or range.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

In accordance with an exemplary embodiment of the present invention, an implant device with an inner lumen is inserted into a patient's joint between the first metatarsal and the cuneiform to restore length and to provide correction in the medial to lateral direction as well as the dorsal to plantar direction. The implant is connected to an outrigger system that releasably connects to the implant. The inventive assembly allows a clinician to properly insert a screw through the first metatarsal, through the lumen of the implant, and into the cuneiform, providing compression across the joint.

Figure 2:
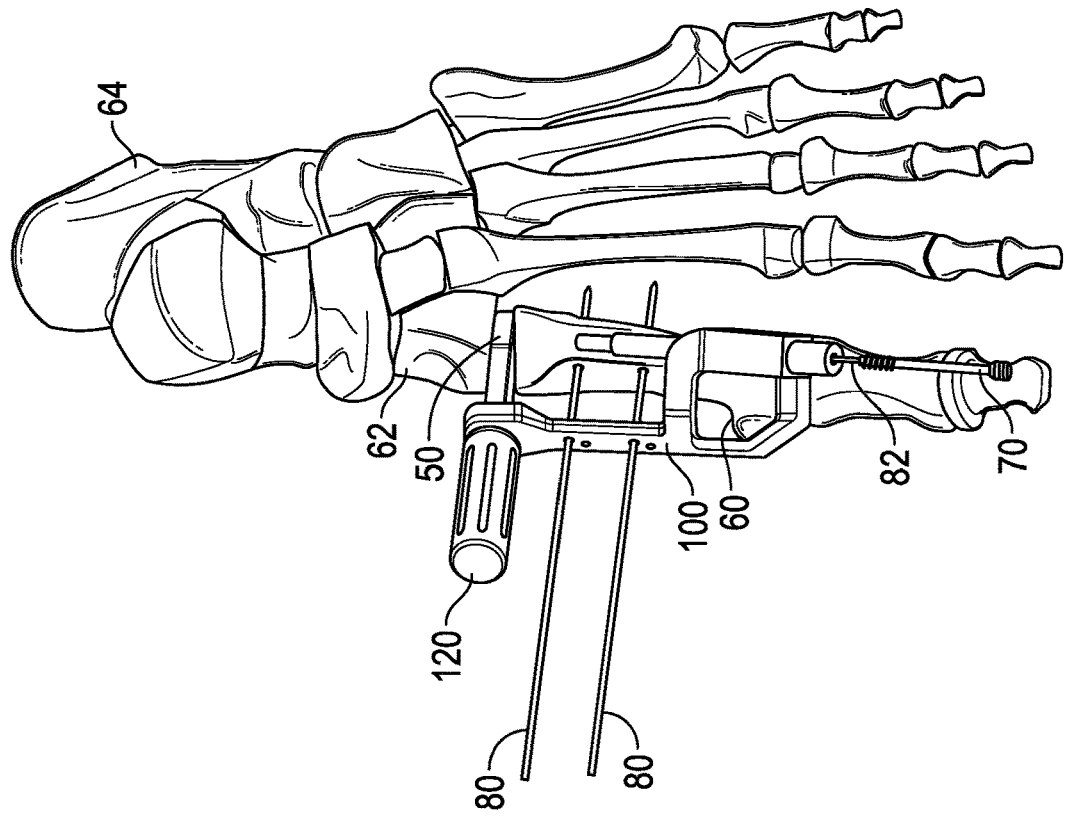
FIG. 2 is a top plan view of the assembly and foot of FIG. 1.
Figure 6:
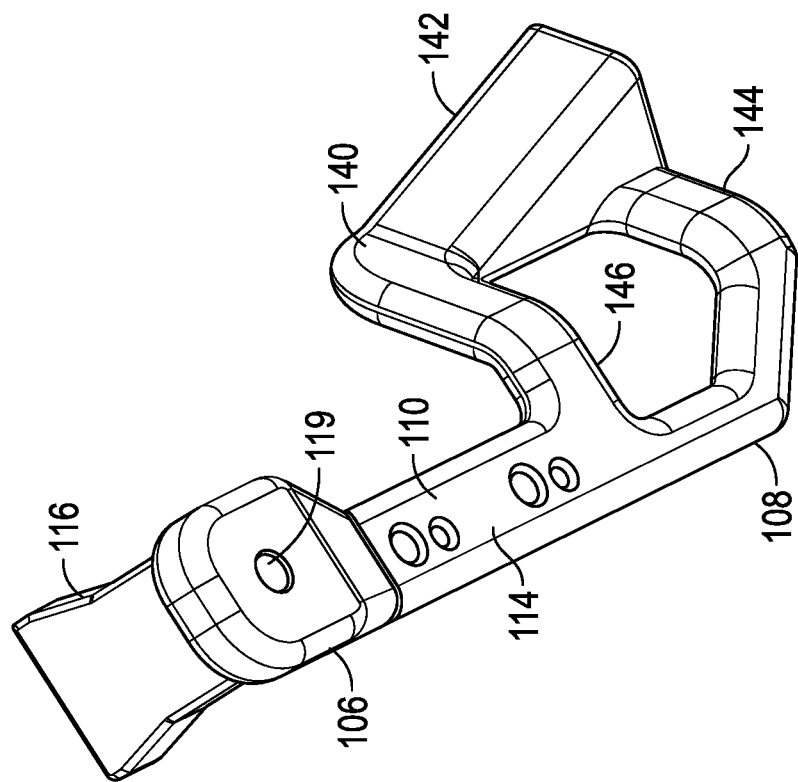
FIG. 6 is a proximal perspective view of the screw guide of FIG. 3.
Figure 5:
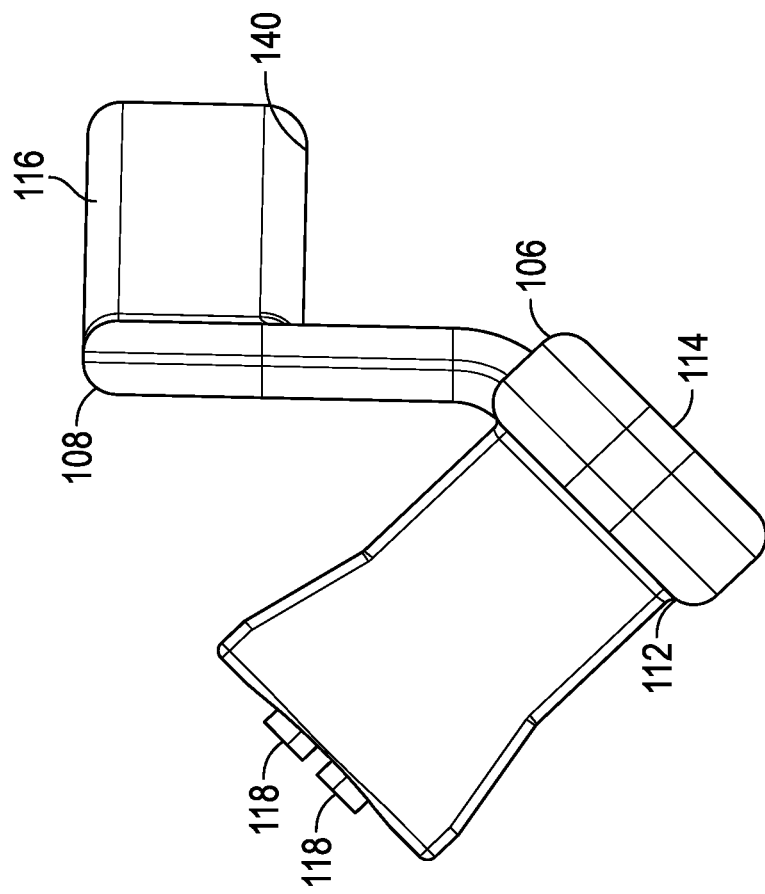
FIG. 5 is a proximal end view of the screw guide of FIG. 3.

Referring to FIGS. 1 and 2, a Lapidus screw guide assembly 100 ("assembly 100") according to an exemplary embodiment of the present invention is shown, attached to an implant 50 that is inserted between a first metatarsal 60 and a cuneiform 62 of a foot 63 (only the bones of foot 63 are shown for clarity). Assembly 100 is used to align a screw 70 for insertion into the first metatarsal 60, through a lumen in implant 50, and into the cuneiform 62.

Referring to FIGS. 3-7, assembly 100 includes a generally planar elongate guide body 102 extending along a central longitudinal axis 104. Guide body 102 has a proximal end portion 106 and a distal end portion 108, distal from proximal end portion 106. Body 102 has a central portion 110 that extends between proximal end portion 106 and distal end portion 108. Body 102 also includes an inferior face 112 and a superior face 114 opposite inferior face 112.

Proximal end portion 106 has an attachment face 116 extending downwardly from inferior face 112 and perpendicular to the longitudinal axis 104 that is adapted to releasably engage and connect to implant 50 (shown in FIG. 10). Attachment face 116 includes a pair of extensions 118 that serve to extend into a slot (not shown) in implant 50 to prevent rotation of implant 50 with respect to attachment face 116. A generally circular through-opening 119 extends through proximal end portion 106, through attachment face 116, and between extensions 118. A threaded opening 121 is formed in proximal end portion 106 and allows for the insertion of a ball plunger (not shown) therein.

Figure 8:
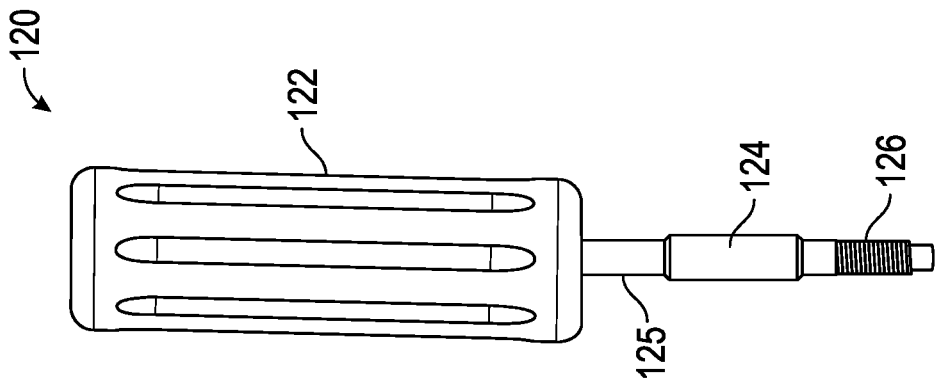
FIG. 8 is a handle for use with the screw guide of FIG. 3.
Figure 7:
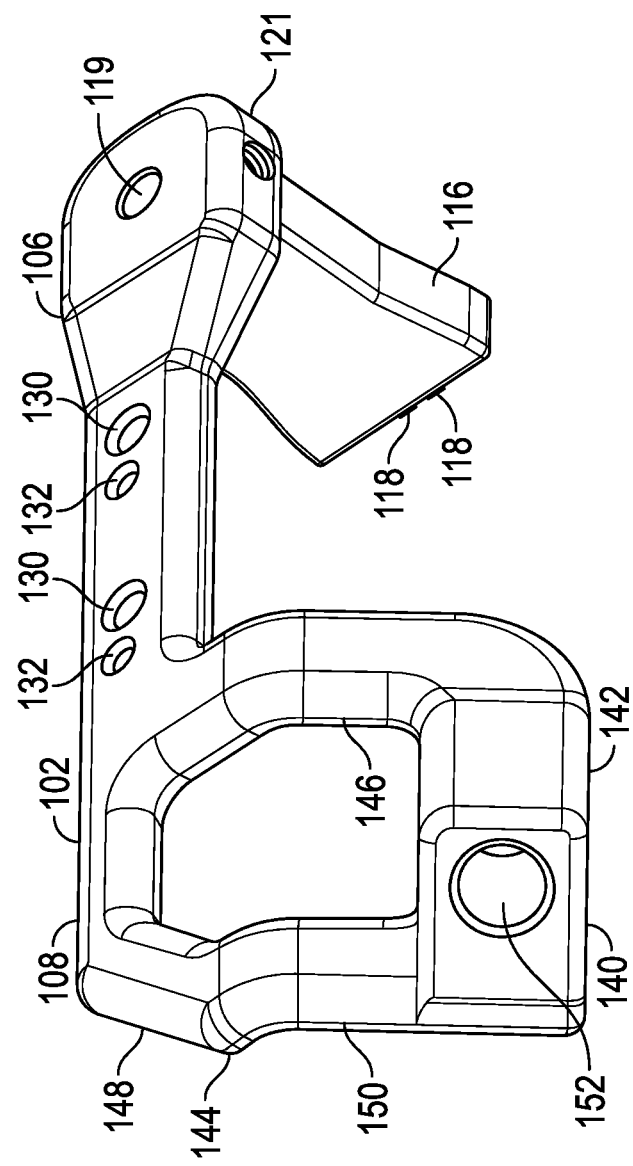
FIG. 7 is a distal perspective view of the screw guide of FIG. 3.

A handle 120, shown in detail in FIG. 8, is rotatably attached to proximal end portion 106. Handle 120 includes a textured knob 122 connected to an unthreaded shaft 124, with a threaded portion 126 extending from shaft 124. FIGS. 1 and 2 show handle 120 extending upwardly from proximal end portion 106.

Shaft 124 has a diameter slightly smaller than the diameter of through-opening 119 and a length slightly longer than the sum of the thickness of proximal end portion 106 and the length of attachment face 116 so that, when shaft 124 is inserted through proximal end portion 106 and attachment face 116 so that handle 120 extends co-linearly with attachment face 116, threaded portion 126 extends outwardly from attachment face 116 for threaded engagement with implant 50. A narrowed shaft portion 125 adjacent to handle 122 allows for the ball plunger described above to engage narrowed shaft portion 125 and retain handle 120 within through-opening 119 while using assembly 100.

Central portion 110 has at least one through-opening 130 extending therethrough from superior face 114 to inferior face 112. As shown in FIG. 4, two through-openings 130 are provide along longitudinal axis 104. Additionally, two additional through-openings 132 are provided co-linearly along an axis parallel to longitudinal axis 104. Through-openings 130 have a larger diameter than through-openings 132 to allow K-wires 80 (shown in FIGS. 1, 2, 20, and 21) having different diameters to be inserted therein with minimal gap between the K-wire 80 and the respective through-openings 130, 132. In an exemplary embodiment, through-openings 130 have a diameter of 2.4 millimeters and through-openings 132 have a diameter of 1.6 millimeters.

Distal end portion 108 has a screw support member 140 that extends away from longitudinal axis 104. Screw support member 140 is configured to allow for the insertion of screw 70 at an angle oblique relative to longitudinal axis 104. Screw support member 140 is supported by an outrigger 142 extending from distal end portion 108. Outrigger 142 has a first arm 144 extending from distal end portion 108 and a second arm 146 disposed proximally of first arm 144 such that first and second arms 144, 146 are each connected to screw support member 140. Referring to FIG. 4, first arm 144 has a first portion 148 extending obliquely from distal end portion 108 and a second portion 150 extending generally orthogonally to distal end portion 108.

Outrigger 142 includes a screw through-opening 152 extending therethrough such that screw through-opening 152 extends obliquely to longitudinal axis 104. Screw through-opening 152 extends at an angle between about 20 degrees and about 30 degrees relative to body 102 and is adapted to guide screw 70 therethrough.

Figure 11:
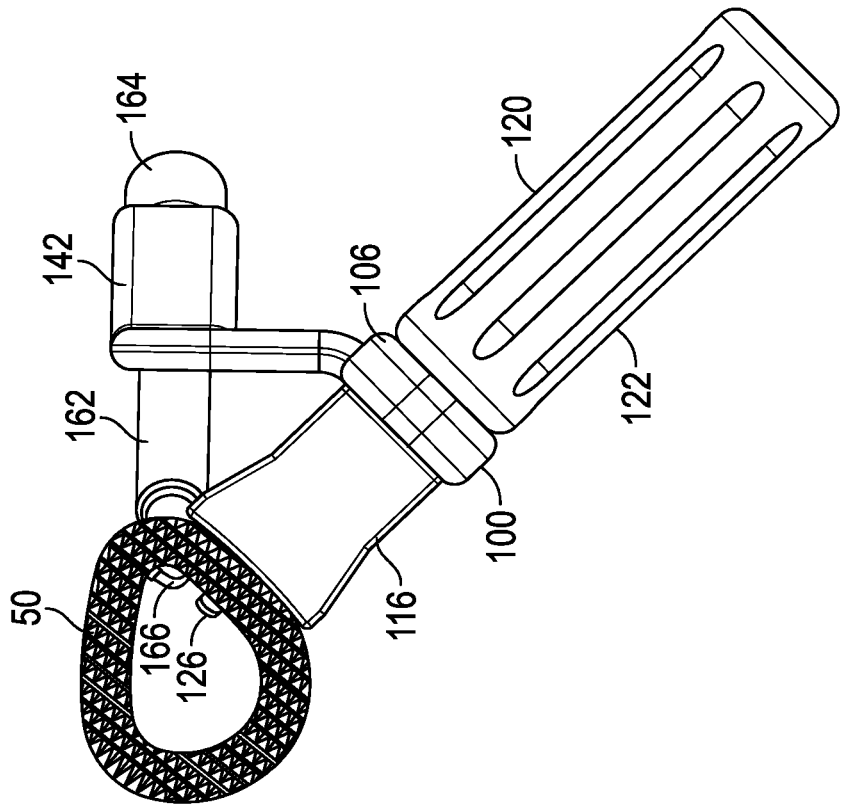
FIG. 11 is a proximal end view of the screw guide assembly with implant of FIG. 10.

A wire guide 160, shown in detail in FIG. 9, can be removably inserted into screw through-opening 152, as shown in FIG. 11. Wire guide 160 is used to guide a K-wire 82 (shown in FIGS. 1, 22, and 23) therethrough to assist in inserting screw 70.

Wire guide 160 has a generally cylindrical, elongate body 162 with a head 164 having a diameter larger than the diameter of screw through-opening 152 so that head 164 prevents wire guide 160 from sliding all the way through screw through-opening 152. Wire guide 160 has a narrow bottom end to provide stability to the bone that wire guide 160 is intended to contact. Additionally, a plurality of teeth 167 are cut into bottom end 166 to provide an engagement surface for to bone. A K-wire passage 168 extends longitudinally through wire guide 160 from head 164 to bottom end 166 to allow K-wire 82 to be inserted therethrough.

Figure 12:
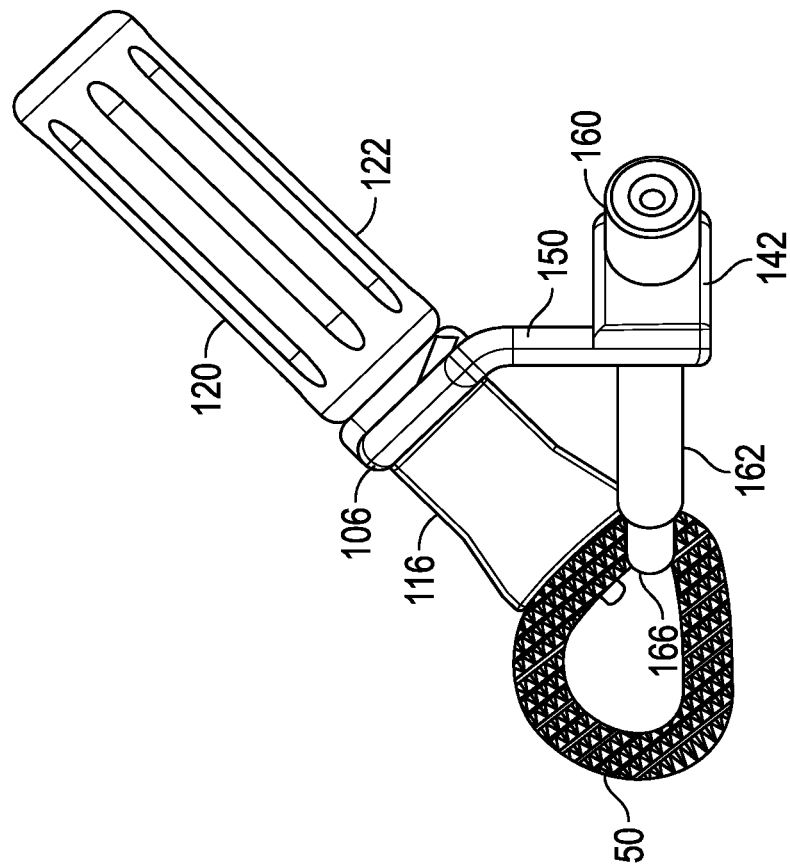
FIG. 12 is a distal end view of the screw guide assembly with implant of FIG. 10.

In an exemplary embodiment, body 102, attachment face 116, and wire guide 160 can be constructed from stainless steel, although those skilled in the art will recognize that these members can be constructed from other, rigid materials such as, for example, a rigid polymer. Assembly 100 with implant 50 attached to attachment face 116 is shown in FIGS. 10-12.

Figure 13:
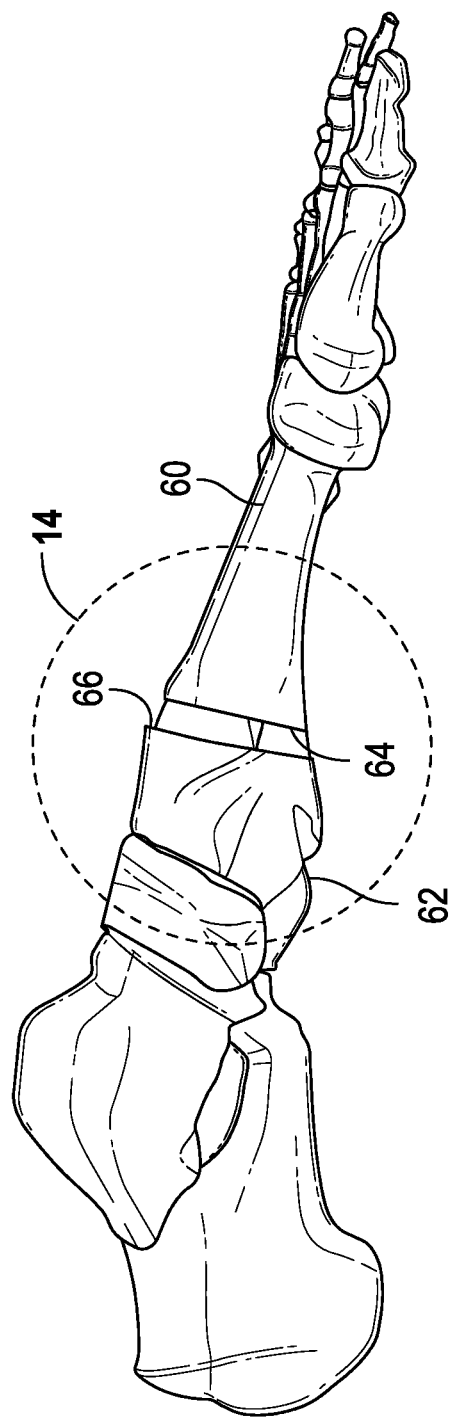
FIG. 13 is a side elevational view of a foot bone with an osteotomy.
Figure 14:
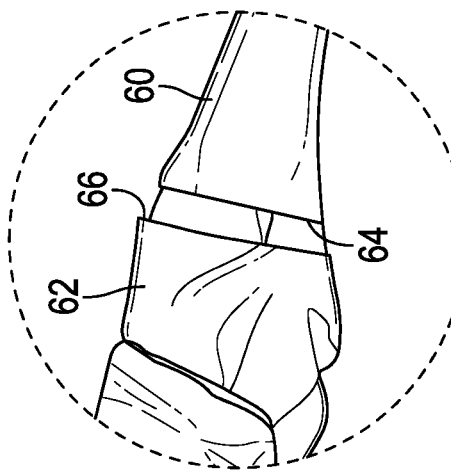
FIG. 14 is an enlarged view of the osteotomy site taken along circle 14 of FIG. 13.

FIGS. 13-28 show graphical illustrations of an exemplary method to use assembly 100 to insert an implant. First, as shown in FIGS. 13 and 14, fusion cuts 64, 66 are made parallel to the first tarsometatarsal ("TMT") joint if implant 50 is an angled wedge. If a parallel sided implant is used, the fusion cut sites should be angled for desired correction.

Figure 16:
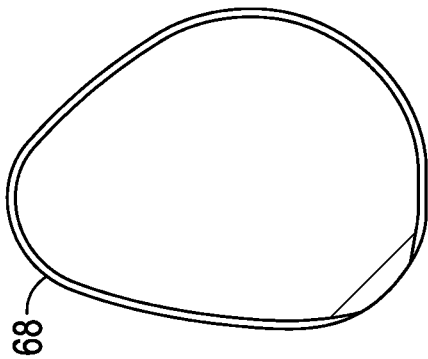
FIG. 16 is a proximal elevation view of the trial head of FIG. 15.
Figure 15:
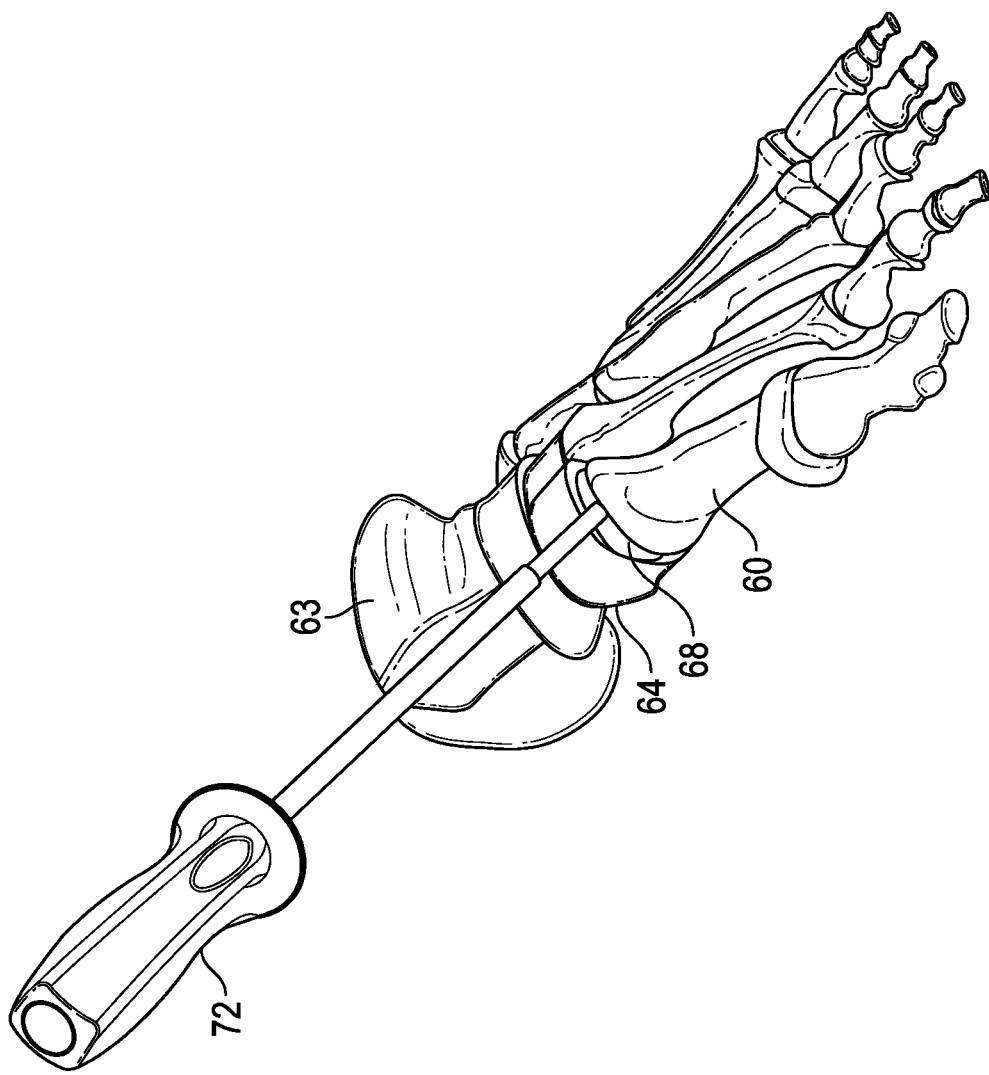
FIG. 15 is a perspective view of a trial head being inserted into the osteotomy site of FIG. 13.
Figure 18:
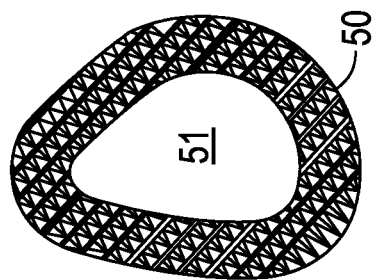
FIG. 18 is a proximal elevational view of the implant of FIG. 17.
Figure 17:
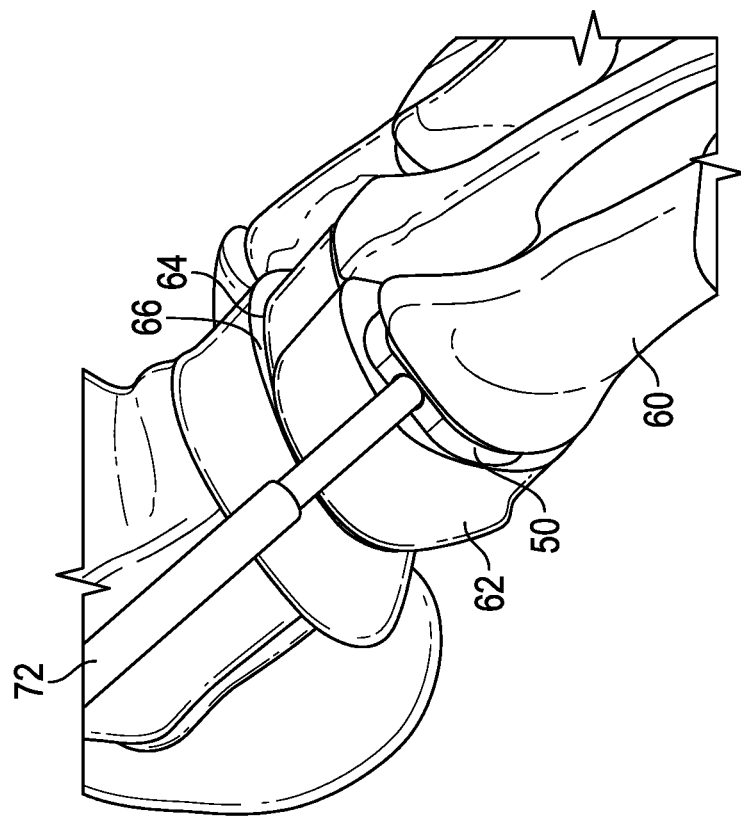
FIG. 17 is a perspective view of an implant being inserted into the osteotomy site.

Next, as shown in FIGS. 15 and 16, trial heads 68 are attached to an inserter 72 and test inserted into the space formed between fusion cuts 64, 66 until a desired size/shape implant 50 is located. Exemplary implants can be found in U.S. patent application Ser. No. 15/646,497, which is owned by the owner of the present application. As shown in FIGS. 17 and 18, once a desired implant 70 is selected, implant 70 is attached to inserter 72 and inserted into the space between fusion cut sites 64, 66. FIG. 18 shows implant 50 having a lumen 51 formed therein.

Figure 20:
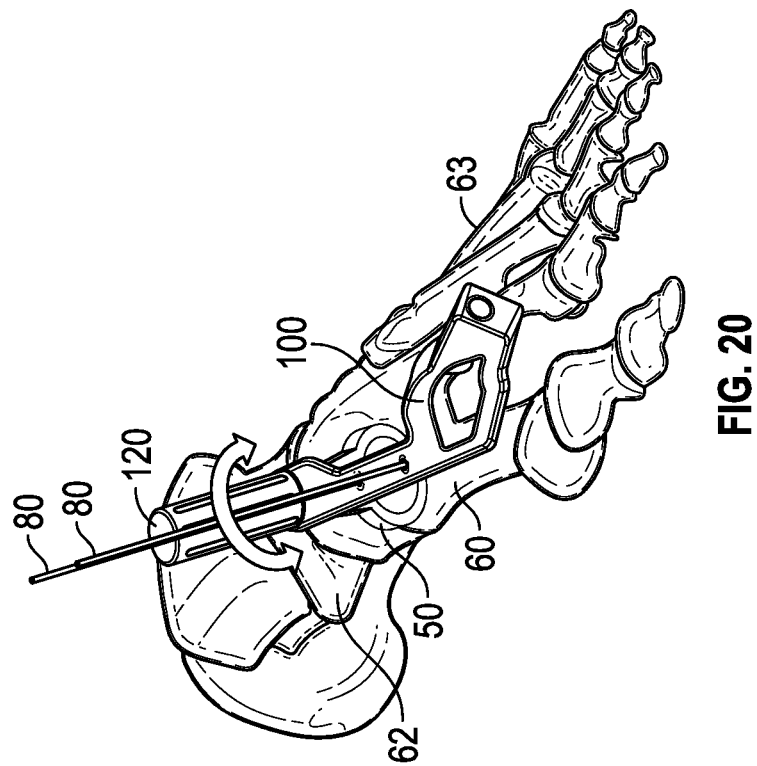
FIG. 20 is a perspective view of the screw guide assembly with stabilizing K-wires being used to rotate the metatarsal relative to the rest of the foot.
Figure 19:
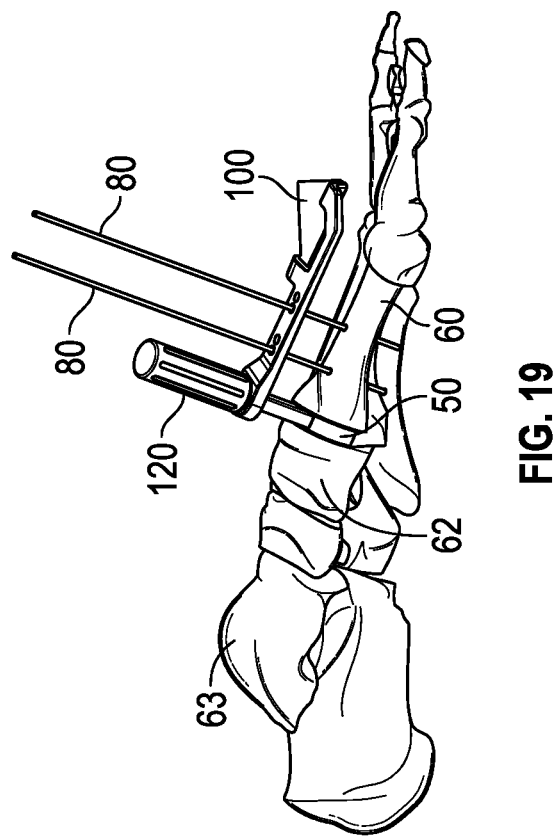
FIG. 19 is a side elevational view of the screw guide assembly of FIG. 3 with the implant of FIG. 18 inserted into the first metatarsal and stabilizing K-wires inserted through the central portion of the screw guide assembly and into a metatarsal.

As shown in FIG. 19, assembly 100 is attached to implant 50. Assembly 100 is attached by inserting threaded end 126 of handle 120 through distal end portion 108 and attachment face 116 so that threaded end 126 can thread into implant 50. K-wires 80 are inserted through through-openings 130 and into first metatarsal 60. FIG. 20 show the ability to rotate first metatarsal 60 relative to cuneiform 62 by using handle 120 as a lever to rotate assembly 100 and K-wires 80.

Figure 22:
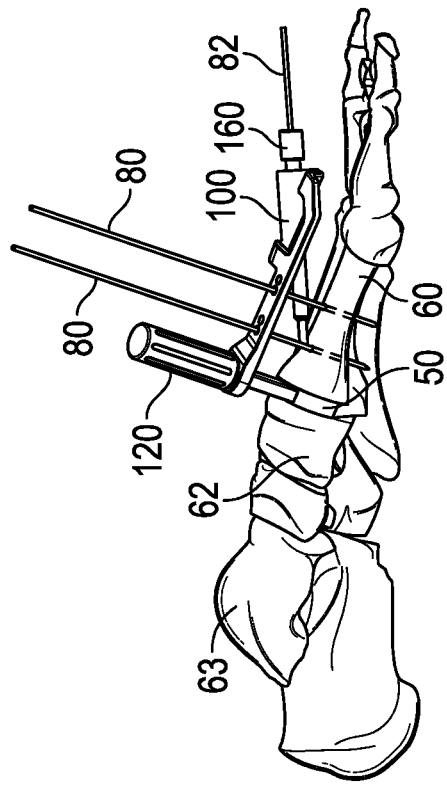
FIG. 22 is a side elevational view of a K-wire being inserted into the wire guide.
Figure 21:
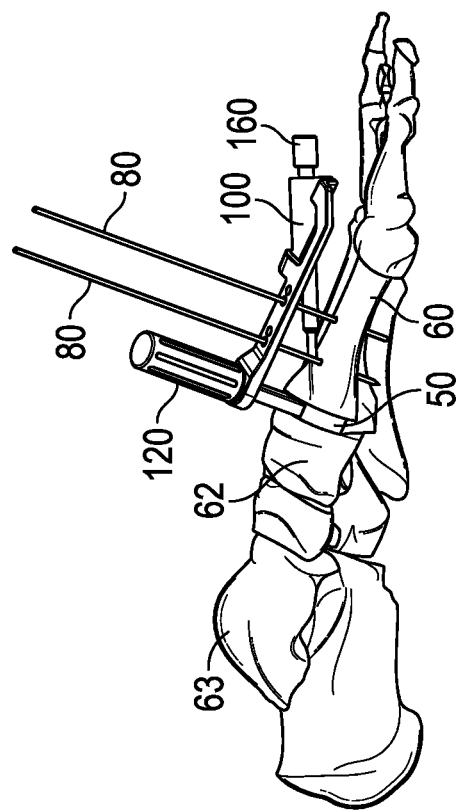
FIG. 21 is a side elevational view of the screw guide assembly with the wire guide inserted into the outrigger.

As shown in FIG. 21, wire guide 160 is next removably inserted into screw through-opening 152 and, as shown in FIG. 22, a K-wire 82 is inserted through through-opening 168. K-wire 82 extends through first metatarsal 60, through lumen 51 in implant 50, and into cuneiform 62. FIG. 23 shows a drill 84 inserted over the distal end of K-wire 82 to drill a passage for the insertion of screw 70.

Figure 26:
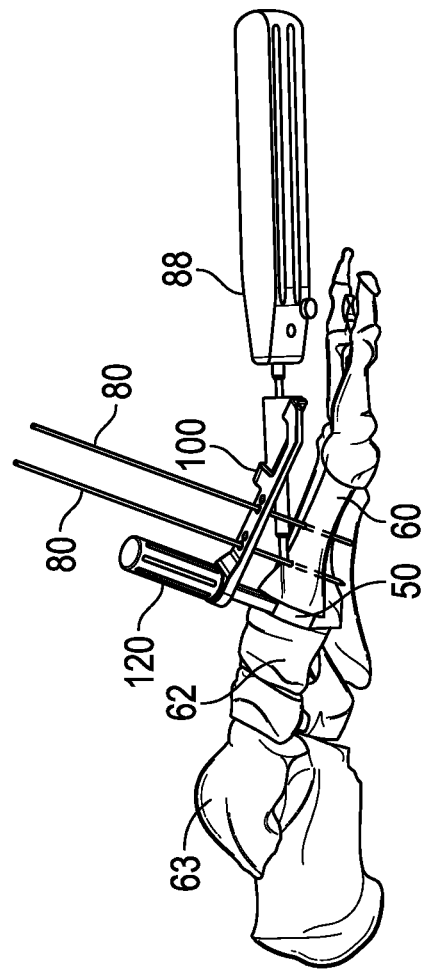
FIG. 26 is a side elevational view of a driver used to screw the screw into the bones.
Figure 25:
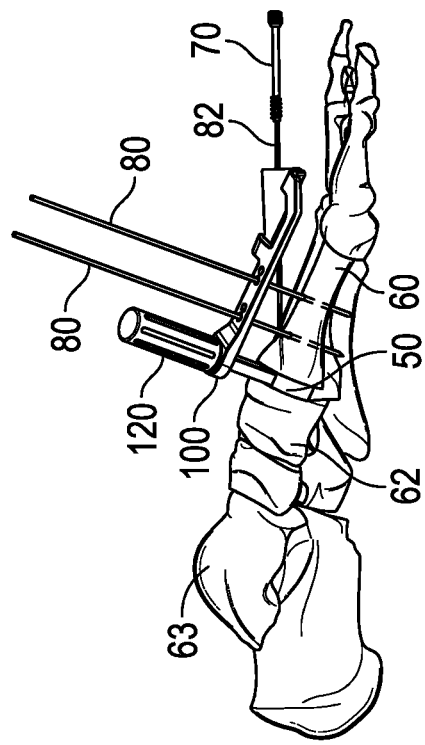
FIG. 25 is a side elevational view of a screw being slid over the K-wire.

Optionally, as shown in FIG. 24, assembly 100 can be removed, leaving K-wire 82 in place, and sliding a countersink bit 86 over K-wire 82 to drill a countersink passage. If countersink bit 86 is used, afterward, assembly 100 is reinstalled as shown in FIG. 25, and screw 70 is sild over K-wire 82. FIG. 26 shows a driver 88 slid over K-wire 82 to drive screw 70 into first metatarsal 60, through lumen 51 in implant 50, and into cuneiform 62.

Figure 28:
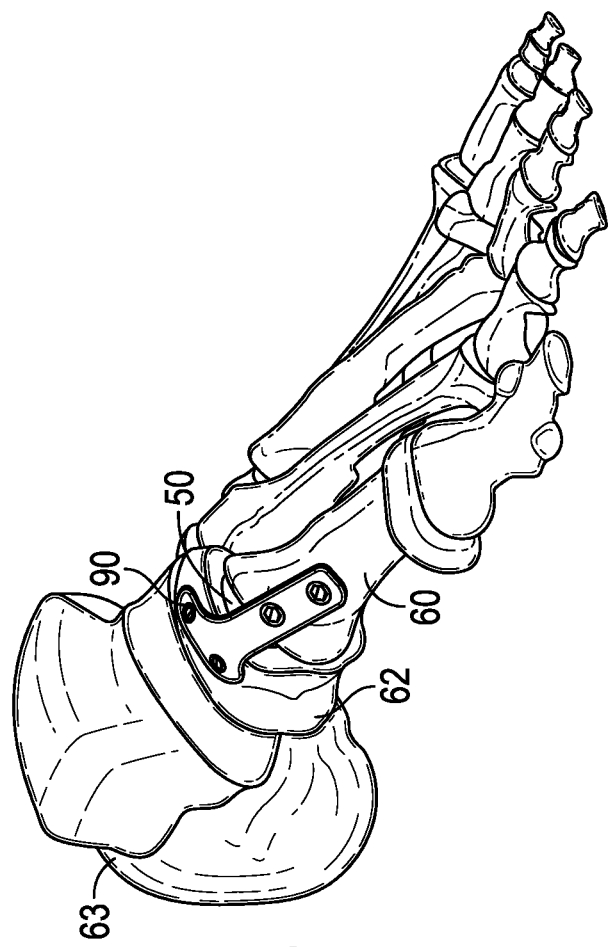
FIG. 28 is a perspective view of a plate having been connected to the metatarsal and the cuneiform to retain the implant in place.
Figure 27:
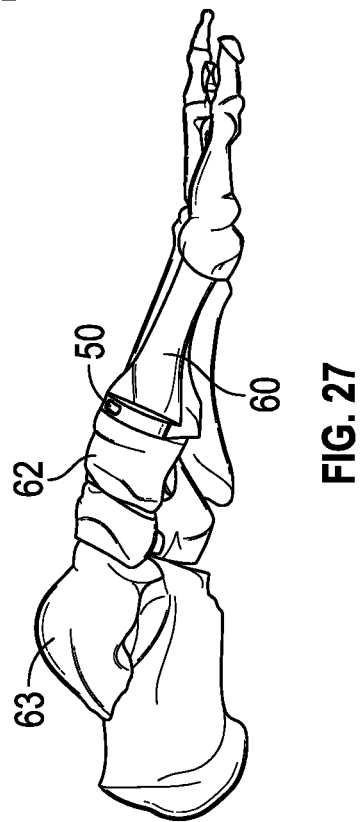
FIG. 27 is a side elevational view of the screw inserted into the first metatarsal and the cuneiform, with the screw guide assembly having been removed from the implant.

After screw 70 is inserted, assembly 100 is removed, as shown in FIG. 27. Optionally, as shown in FIG. 28, a plate 90 can be secured to first metatarsal 60 and cuneiform 62, over implant 50, to secure implant 50 in place.

It will be further understood that various changes in the details, materials, and arrangements of the parts which have been described and illustrated in order to explain the nature of this invention may be made by those skilled in the art without departing from the scope of the invention as expressed in the following claims.

We claim:
1. A method of moving a joint, comprising the steps of:
   (a) placing a screw guide assembly over a first metatarsal of a foot;
   (b) inserting a first wire through the screw guide assembly and into the first metatarsal;
   (c) rotating the first metatarsal relative to a cuneiform; and
   (d) fixing the first metatarsal to the cuneiform,
      wherein step (d) comprises inserting a wire guide through the screw guide assembly to the first metatarsal and after inserting the wire guide through the screw guide assembly to the first metatarsal, inserting a K wire through the wire guide, into the first metatarsal, and into the cuneiform.

2. The method according to claim 1, further comprising the step of, prior to step (a), attaching the screw guide assembly to an implant.

3. The method according to claim 2, further comprising the step of, prior to attaching the screw guide assembly to the implant, implanting the implant between the first metatarsal and the cuneiform.

4. The method according to claim 1, wherein step (b) further comprises inserting a second wire through the screw guide assembly and into the first metatarsal.

5. The method according to claim 1, wherein the screw guide assembly comprises a handle and wherein step (c) comprises grasping and rotating the handle to rotate the screw guide assembly.

6. The method according to claim 1, wherein step (d) further comprises, after inserting the K wire through the wire guide, into the first metatarsal, and into the cuneiform, inserting a screw over the K wire through the first metatarsal and the cuneiform.

7. The method according to claim 1, further comprising, after step (c) and before step (d), the steps of:
(c1) removing the assembly, and leaving the K-wire in place;
(c2) sliding a countersink bit over the K-wire and drilling a countersink passage; and
(c3) reinstalling the assembly.

8. The method according to claim 1, wherein step (d) comprises inserting a screw through the first metatarsal and into the cuneiform.

9. The method according to claim 1, further comprising the step of:
(e) attaching a plate to the first metatarsal and the cuneiform.

10. A method of moving a joint, comprising the steps of:
(a) inserting an implant between a first metatarsal and a cuneiform;
(b) placing a screw guide assembly over the first metatarsal and the implant;
(c) attaching the screw guide assembly to the implant;
(d) inserting a first wire through the screw guide assembly and into the first metatarsal;
(e) rotating the first metatarsal relative to the cuneiform;
(f) fixing the first metatarsal to the cuneiform; and
(g) attaching a plate to the first metatarsal and the cuneiform over the implant.

11. The method according to claim 10, wherein step (a) comprises the step of inserting a wedge implant.

12. The method according to claim 10, wherein step (d) further comprises inserting a second wire through the screw guide assembly and into the first metatarsal.

13. The method according to claim 10, wherein step (e) further comprises rotating the implant.

14. The method according to claim 13, wherein the screw guide assembly comprises a handle and wherein the step of rotating the implant comprises rotating the handle.

15. The method according to claim 10, wherein step (f) comprises the step of inserting a screw through the first metatarsal and the implant and into the cuneiform.

16. The method according to claim 15, wherein the implant comprises a lumen extending therethrough and wherein the step of inserting the screw through the implant comprises inserting the screw through the lumen.

17. The method according to claim 10, further comprising the step of, between steps (e) and (f), the steps of:
(e1) inserting a wire guide through the screw guide assembly to the first metatarsal;
(e2) inserting a K wire through the wire guide, into the first metatarsal, and into the cuneiform;
(e3) sliding a drill over the K wire and drilling a passage in the first metatarsal;
(e4) removing the drill; and
(e5) inserting a screw over the K wire.

* * * * *